US010702693B2

(12) United States Patent
Ho

(10) Patent No.: US 10,702,693 B2
(45) Date of Patent: Jul. 7, 2020

(54) DEVICE FOR PERFORMING ELECTROTHERAPEUTIC MASSAGE ON A PERSON'S HEAD, NECK, AND SHOULDERS

(71) Applicant: Hoi Ming Michael Ho, Ontario (CA)

(72) Inventor: Hoi Ming Michael Ho, Ontario (CA)

( * ) Notice: Subject to any disclaimer, the term of this patent is extended or adjusted under 35 U.S.C. 154(b) by 611 days.

(21) Appl. No.: 15/604,695

(22) Filed: May 25, 2017

(65) Prior Publication Data
US 2018/0318581 A1 Nov. 8, 2018

(30) Foreign Application Priority Data

May 3, 2017 (TW) .............................. 106114672 A

(51) Int. Cl.
A61N 1/04 (2006.01)
A61N 1/32 (2006.01)
A61N 1/36 (2006.01)
A61H 39/04 (2006.01)

(52) U.S. Cl.
CPC ............. A61N 1/322 (2013.01); A61H 39/04 (2013.01); A61N 1/0452 (2013.01); A61N 1/0456 (2013.01); A61N 1/0472 (2013.01); A61N 1/36014 (2013.01); A61N 1/36021 (2013.01); A61H 2201/10 (2013.01); A61H 2205/02 (2013.01); A61H 2205/04 (2013.01); A61H 2205/062 (2013.01); A61N 1/3604 (2017.08)

(58) Field of Classification Search
CPC ...... A61N 1/04; A61N 1/0404; A61N 1/0408; A61N 1/0452; A61N 1/0456; A61N 1/0472; A61N 1/0476; A61N 1/0484; A61N 1/26; A61N 1/322; A61B 5/6801; A61B 5/6802; A61B 5/6803; A61B 5/6804; A61B 5/6812; A61B 5/6813; A61B 5/6814; A61B 5/6822
See application file for complete search history.

(56) References Cited

U.S. PATENT DOCUMENTS

| 5,569,166 | A | * | 10/1996 | Stone | A61H 7/004 601/103 |
| D790,880 | S | * | 7/2017 | Wong | D6/601 |
| D812,238 | S | * | 3/2018 | Ho | D24/200 |
| D818,145 | S | * | 5/2018 | Ho | D24/215 |

(Continued)

Primary Examiner — Eugene T Wu
(74) Attorney, Agent, or Firm — CIPO IP Group

(57) ABSTRACT

A device for performing electrotherapeutic massage on the human head, neck, and shoulders includes an inner core structure, at least four protruding nodules, plural electrical wires, and an outer covering. The inner core structure has a central horizontal accommodating opening for accommodating the neck and plural horizontal cushion openings. The horizontal accommodating opening matches the curvature and alignment of the human cervical spine and the kyphotic curvature of the thoracic vertebrae. Each protruding nodule is made of an electrically conductive fabric and sewn to the wall of the corresponding horizontal cushion opening in order to deliver the electrical nerve stimulation pulses generated by an electrotherapeutic signal generator to the corresponding body portion, thereby relaxing the nerve and muscle groups therein. The electrical wires electrically connect the protruding nodules to the electrotherapeutic signal generator. The outer covering encloses the inner core structure while exposing the protruding nodules.

24 Claims, 6 Drawing Sheets

(56) References Cited

U.S. PATENT DOCUMENTS

| | | | | |
|---|---|---|---|---|
| 2006/0142675 A1* | 6/2006 | Sargent | ............... | A61H 39/04 601/70 |
| 2013/0184621 A1* | 7/2013 | Ma | ...................... | A61H 7/004 601/134 |
| 2014/0083434 A1* | 3/2014 | Groteke | ............ | A61N 1/0476 128/845 |

* cited by examiner

DEVICE FOR PERFORMING ELECTROTHERAPEUTIC MASSAGE ON A PERSON'S HEAD, NECK, AND SHOULDERS

FIELD OF THE INVENTION

The present invention relates to a massage device and more particularly to one configured to perform electrotherapy on a person's head, neck, and shoulders. The massage device disclosed herein not only has a compact, simple, and multifunctional structural design that allows the massage device to be carried around and operated with ease by patients as well as physical therapists wherever desired, but also helps keep the natural lordotic curvature of a patient's cervical spine while conducting electrotherapy on the corresponding important nerves and muscles in the patient's head, neck, and shoulders. By maintaining the natural lordotic curvature, the effect of electrotherapeutic massage on a patient's head, neck, and shoulders will be effectively enhanced so that pain can be precisely and efficiently relieved from the patient's head, neck, and shoulders. Also, the related muscle groups in the patient's head, neck, and shoulders will be able to relax, thereby fine-tuning the corresponding portion of the vertebral column to its proper position.

BACKGROUND OF THE INVENTION

The human body is a structure that constitutes a subtle and complicated electric field environment, consisting of approximately 60 trillion cells, on which the organs in the body depend for metabolism and regeneration on a daily basis in order to maintain the phenomena and functions of life. The metabolism of cells involves a great variety of mineral ions. For example, potassium ions in the intracellular fluid exchange with sodium ions in the extracellular fluid within one hundredth of a second, generating an electric potential generally known as the "action potential". When the electric potential of the human body is in equilibrium, physical health ensues, and from the perspective of traditional Chinese medicine, such equilibrium is a harmony between qi and blood, or yin and yang. Conversely, failure to keep the electric potential of the human body in equilibrium leads to diseases. In fact, medical science has proved that the impedance of certain points on a person's skin drops when the person falls ill, and this clinical observation is in line with the theory of "acupuncture points" in traditional Chinese medicine. From the physiological point of view of traditional Chinese medicine, there are about 730 acupuncture points distributed over the entire human body. The acupuncture points are the foundation of acupuncture, which is a treatment based on the "salt bridge theory", according to which electrical connection (i.e., ion exchange) between at least two metal needles inserted in the skin can activate related cells, stimulate the meridian system, and bring about normal physiological functions of the body. Nowadays, all the electrotherapy devices on the market are applications of Chinese acupuncture, the first ones being invented by Dr. Yoshio Nakatani, a doctor of medicine of Japan. With continued research and development efforts and incessant improvement, such devices have been able to promote blood circulation as well as metabolism and are in extensive use in hospitals and homes due to their effectiveness, safety, and zero side effects. In Japan, the US, and many European countries, electrotherapy devices have even become essential household devices for health maintenance. Typically, referring to FIG. 1, a conventional electrotherapy device 10 includes an electrotherapeutic signal generator 15 (e.g., a transcutaneous electrical nerve stimulator (TENS) or electronic muscle stimulator (EMS)) and a plurality of electrode pads 12. The electrotherapeutic signal generator 15 is configured to generate a series of electrical nerve stimulation pulses. Each electrode pad 12 includes an electrode 121 coated at one end with a thin film of self-adhering water-based silicone gel 122 so that the end of the electrode 121 can be adhesively attached to an acupuncture point on a patient's head, neck, or shoulders via the silicon gel 122. The opposite end of each electrode 121 is electrically connected to the electrotherapeutic signal generator 15 through a conductive wire 13 in order to receive the electrical nerve stimulation pulses generated by and sent from the electrotherapeutic signal generator 15 and deliver the pulses to the corresponding acupuncture point on the patient's head, neck, or shoulders through the aforesaid end of the electrode 121 and the silicon gel 122 coated thereon. The conventional electrotherapy device 10 can therefore perform an effective electrotherapeutic massage on the intended acupuncture points on the patient's head, neck, and shoulders to relieve pain from those body parts. Depending on the range of current frequency of the electrical nerve stimulation pulses generated by the electrotherapeutic signal generator 15, the conventional electrotherapy device 10 can be categorized as low-frequency or medium-frequency. With continued reference to FIG. 1, a low-frequency electrotherapy device 10 refers to an electrotherapy device whose electrotherapeutic signal generator 15 generates electrical nerve stimulation pulses of a current frequency ranging from 2 Hz to 150 Hz. Such low-frequency electrical nerve stimulation pulses can directly stimulate and excite muscle and nerve groups about 1 cm below the dermal tissues as a way to treat diseases associated with epidermal nerves or muscles. In addition to providing a general pain-relieving or anesthetic effect on superficial muscles, this type of electrical nerve stimulation pulses can promote blood circulation in the skin and improve nutrient transport in related tissues. However, as low-frequency electrical nerve stimulation pulses tend to stimulate cortical neurons to a relatively great extent and thus cause pain in the skin, it is generally infeasible to apply a high dosage of current to the patient, and the result is hence limited. Moreover, the high impedance of the human skin to low-frequency electrical nerve stimulation pulses makes it difficult for those pulses to pass through the skin and work on deeper tissues. In particular, low-frequency electrical nerve stimulation pulses tend to cause electrolysis beneath the electrodes and thus burn the skin tissues. In a nutshell, the foregoing drawbacks of low-frequency electrical nerve stimulation pulses prevent long-term high-dosage treatment.

On the other hand, referring back to FIG. 1, a medium-frequency electrotherapy device 10 is an electrotherapy device whose electrotherapeutic signal generator 15 generates electrical nerve stimulation pulses of a current frequency ranging from 1 kHz to 5 kHz. Such medium-frequency electrical nerve stimulation pulses have been used in physical therapy to provide electrical stimulation, or more particularly to carry out an intended treatment through the interference waves generated by two different medium-frequency electric stimulants (the working principle of which is similar to that of beat generation by two signals of different frequencies). This kind of treatment, therefore, is also known as interference-wave therapy or interference-current therapy (or IFC therapy for short). The interference current generated by medium-frequency electrical nerve stimulation pulses can be used to simulate nerves, trigger alternate involuntary contraction and relaxation of muscles, and thereby perform the following treatments:

1. To kill pain by interfering with the pain signal transmission of nerves and by stimulating the secretion of endorphins.

2. To promote blood circulation and reduce edema of the limbs.

3. As medium-frequency electrical nerve stimulation pulses can be used at a high dosage, can penetrate deep to the origin of pain, have low interference, and can help heal body tissues, they are highly suitable for clinical treatment of the following sports injury symptoms: muscle strain, contusion, degenerative arthritis, pain in the lower back, and so on. Furthermore, medium-frequency electrical nerve stimulation pulses, whose current waveform can reach tissues about 6~9 cm deep from the skin, have good therapeutic effect on acute and chronic inflammation, swelling, and pain.

4. To promote blood circulation and lymph return, improve tissue nutrition, and accelerate self-healing of wounds and bones.

5. Now that the human skin has low impedance to medium-frequency electrical nerve stimulation pulses, it is easy for the current of such pulses to enter body tissues, and there will be no stinging sensation in the skin. Besides, medium-frequency electrical nerve stimulation pulses do not have an electrolytic effect on the human body and hence will not injure the skin and its tissues. These merits allow patients to receive high-dosage treatment with medium-frequency electrical nerve stimulation pulses for a long time.

In consideration of the above, medium-frequency electrotherapy devices have been widely used to perform electrotherapeutic massage on people's heads, necks, shoulders, and backs, with a view to relaxing the related muscle groups and relieving pain from those body parts. Nevertheless, referring again to FIG. 1, patients and physical therapists who perform electrotherapeutic massage on the head, neck, shoulders, and back using the conventional medium-frequency electrotherapy device 10 are almost certain to encounter the following inconveniences and problems that hinder the medium-frequency electrotherapy device 10 from delivering the medium-frequency electrical nerve stimulation pulses steadily and precisely to, i.e., from performing an effective electrotherapeutic massage on, the intended acupuncture points on the head, neck, and shoulders. In the end, unsatisfactory results reduce the users' willingness to use the medium-frequency electrotherapy device 10 again, giving rise to a wasteful use of resources.

(1) While the electrodes 121 of the electrode pads 12 of the conventional medium-frequency electrotherapy device 10 are designed for adhesive attachment to the intended acupuncture points on a patient's head, neck, and shoulders through the thin films of self-adhering water-based silicon gel 122 coated respectively on the electrodes 121, the adhesive attachment surface of each thin film of self-adhering water-based silicon gel 122 does not match the skin surface of each acupuncture point on a patient's head, neck, and shoulders. More specifically, the former surface is a flat plane, but the latter surface, a curved one. It follows that adhesive attachment between the electrode pads 12 and the skin surfaces of the intended acupuncture points on a patient's head, neck, and shoulders may be insecure; that is to say, it is likely that the electrodes 121 are not precisely in contact with the skin surfaces of the intended acupuncture points on the patient's head, neck, and shoulders. Should this happen, the expected therapeutic effect will not be achieved.

(2) During an electrotherapeutic massage session, the electrical nerve stimulation pulses generated by the electrotherapeutic signal generator 15 of the conventional medium-frequency electrotherapy device 10 produce an interference current that stimulates the nerves, causing muscles under the intended acupuncture points on the patient's head, neck, and shoulders to contract and relax alternately in an involuntary manner. Such alternate involuntary muscle contraction and relaxation may lead to detachment, and consequently inactivity, of the electrode pads 12, which may be only loosely attached to the intended acupuncture points on the patient's head, neck, and shoulders in the first place, resulting in accidental termination of the electrotherapeutic massage session.

(3) The thin films of self-adhering water-based silicon gel 122 are a self-adhering water-based material that is sticky only when moist. When the silicon gel 122 has been adhesively attached to the intended acupuncture points on a patient's head, neck, and shoulders for a considerable amount of time or has been used repeatedly in several massage sessions, it tends to dry out due to loss of moisture and thus lose its self-adhesiveness. This phenomenon is particularly evident and serious on patients with dry or hairy skin.

(4) Generally speaking, most patients are unfamiliar with the medical principles of acupuncture points and know little about the importance of positional accuracy of acupuncture points in relieving pain from the head, neck, or shoulders. Consequently, a patient performing electrotherapeutic massage on themselves is very likely to massage the wrong spots such that not only is the intended therapeutic effect not achieved, but also the patient's head, neck, or shoulders may be injured.

(5) Traditionally, a patient receiving electrotherapeutic massage on the head, neck, and shoulders assumes a sitting position, in which the neck supports the weight of the head (about 10~12 pounds for adults) completely. In other words, the patient's neck will naturally exert a certain force to keep the head upright during the electrotherapeutic massage session. With the patient's neck muscles in tension, however, the expected therapeutic effect cannot be attained.

(6) To prevent the electrode pads 12 from peeling off the corresponding acupuncture points on the neck during an electrotherapeutic massage session, the patient being massaged tends to make a special effort to keep the neck still, but this special effort will strain the neck muscles even more, making it impossible to relax those muscles.

(7) Since most patients receiving electrotherapeutic massage would strive to keep their heads and necks erect and still during the entire massage session, it is all too natural that the patients occasionally turn their heads sideways to relax the tight muscles in their necks and shoulders. Such turns may nevertheless cause the electrode pads 12 to detach from the corresponding acupuncture points on a patient's head, neck, and shoulders, thereby rendering the electrode pads 12 inactive and stopping the massage session prematurely.

(8) If, during an electrotherapeutic massage session, the patient attempts to secure the electrode pads 12 at the intended acupuncture points on the head, neck, and shoulders with their hands, the muscles below the acupuncture points will tighten up because of the lifted arms, thus hampering the expected therapeutic effect.

(9) To address the issue that the silicon gel 122 coated on the electrode pads 12 may end up useless due to loss of self-adhesiveness, disposable electrode pads 12 for a single use were developed. As such disposable electrode pads 12 can be used only once and must be discarded after use, an unnecessary waste of resources takes place, and the large expenses incurred place a heavy financial burden on those who need electrotherapeutic massage.

(10) Owing to the drawbacks and inconveniences stated above, patients and physical therapists who receive or perform electrotherapeutic massage on the head, neck, shoulders, and back via the medium-frequency electrotherapy device 10 often have problem delivering medium-frequency electrical nerve stimulation pulses precisely to the intended acupuncture points on the aforesaid body parts, meaning the acupuncture points are massaged ineffectively. This kind of experience will dampen the users' willingness to continue using the medium-frequency electrotherapy device 10, leading to a waste of resources, which is truly a shame.

In the light of the above, it is important to develop a novel massage device that is configured to perform electrotherapeutic massage on a patient's head, neck, and shoulders; whose compact, simple, and multifunctional structural design allows the massage device to be carried around and operated with ease by patients and physical therapists alike wherever desired; and that helps maintain the natural lordotic curvature of a patient's cervical spine while performing electrotherapeutic massage precisely on the corresponding important acupuncture points on the patient's head, neck, and shoulders, thereby relaxing the nerve and muscle groups beneath the corresponding important acupuncture points; relieving pain from the patient's head, neck, and shoulders precisely and efficiently; reducing muscle tightness in the aforesaid body parts; and by means of the foregoing muscle relaxing mechanism, fine-tuning the corresponding portion of the vertebral column, including the thoracic vertebrae, to its proper position.

BRIEF SUMMARY OF THE INVENTION

To overcome the various drawbacks and inconveniences of the conventional electrotherapy devices, the inventor of the present invention conducted extensive research and repeated trials and finally succeeded in developing a device for performing electrotherapeutic massage on a person's head, neck, and shoulders as disclosed herein. Thanks to its compact, simple, and multifunctional structural design, the disclosed device can be carried around and operated with ease by patients and physical therapists wherever desired. Also, the disclosed device can carry out an effective electrotherapeutic massage precisely on the nerve and muscle groups underneath the corresponding important acupuncture points on a patient's head, neck, and shoulders, thus relieving pain precisely and efficiently from the patient's head, neck, and shoulder muscles. Furthermore, the muscle relaxing mechanism of the present invention makes it possible to fine-tune the corresponding cervical vertebrae and thoracic vertebrae to their proper positions.

It is an objective of the present invention to provide a device for performing electrotherapeutic massage on a person's head, neck, and shoulders. The electrotherapeutic massage device can be electrically connected to an electrotherapeutic signal generator (e.g., a TENS or EMS) in order to receive the electrical nerve stimulation pulses generated by the electrotherapeutic signal generator and deliver those pulses to the corresponding important acupuncture points on the patient's head, neck, and shoulders, thereby conducting a precise and efficient electrotherapeutic massage on the corresponding important acupuncture points on the patient's head, neck, and shoulders to relieve pain from those body parts rapidly. The device includes an inner core structure, at least four protruding nodules, a plurality of electrical wires, and an outer covering. The inner core structure is made of a special blend of foam materials and is centrally formed with a horizontal accommodating opening. The horizontal accommodating opening is configured to match the natural curvature and alignment of the person's cervical spine and has an accommodating curvature matching the kyphotic curvature of the person's thoracic vertebrae so that the person's neck can be stably and comfortably accommodated in the horizontal accommodating opening. In addition, the inner core structure has a posterior portion adjacent to its rear side, and the inner side of the posterior portion is configured to lie against a supporting area of the person's neck. The inner core structure further has two side arms configured to be pressed against supporting areas of the person's shoulders respectively. The inner core structure can be freely compressed or freely expand during use in order for the person's cervical spine to flex, extend, and thereby maintain the natural alignment, and to also maintain the natural lordotic curvature when the electrotherapeutic massage is performed, thus effectively enhancing the effect of the electrotherapeutic massage on the person's head, neck, and shoulders. The inner core structure further includes at least two vertical cushion openings and a plurality of horizontal cushion openings. The vertical cushion openings are vertically formed in the posterior portion of the inner core structure so that the posterior portion of the inner core structure can be deformed and displaced in a forward or rearward direction, allowing the inner core structure to effectively absorb the pressure applied thereby to the person's neck when the inner side of the posterior portion of the inner core structure is pressed tightly against the person's neck. The horizontal cushion openings, on the other hand, are horizontally formed in each of the side arms and the posterior portion of the inner core structure so that the inner core structure can provide sufficient ventilation to ensure that the person's neck feels cool and comfortable when the electrotherapeutic massage is performed on the person. The horizontal cushion openings also allow the side arms and the posterior portion to be deformed and displaced arbitrarily to form a configuration matching the contours of the person's neck and shoulders, thereby providing additional and comfortable cushion and support for the person's head, neck, and shoulders. The protruding nodules, each made of an electrically conductive fabric, have a higher hardness than the inner core structure. Each of the protruding nodules has a periphery sewn to the wall of, or embedded in, the corresponding horizontal cushion opening. Each of the electrically conductive fabrics has a side protruding toward the horizontal accommodating opening such that each of the protruding nodules has a stable and robust configuration and can make comfortable contact with the skin of the person's neck to enable proper current conduction between each of the electrically conductive fabrics and the skin of the person's neck, allowing the electrical nerve stimulation pulses received from the electrotherapeutic signal generator to be delivered through each of the protruding nodules to the corresponding portion of the person's neck, thereby relaxing the muscles in the corresponding portion of, and relieving pain from, the person's neck. More specifically, the protruding nodules are provided on the inner side of the posterior portion of the inner core structure and correspond in positions respectively to the cervical nerves C-1, C-2, and C-7 and the thoracic nerve T-1 (which emerge from the spine bilaterally between the person's upper thoracic spine portion and the suboccipital region at which the posterior hairline is commonly positioned). Thus, when the inner core structure pushes the protruding nodules and thereby presses the electrically conductive fabric of each of the protruding nodules against the skin of the corresponding portion of the person's head, neck, and shoulders, a precise and efficient electrotherapy as well as acupressure therapy is applied to the nerves and the acupuncture points of each of the corresponding portions of the person's head, neck, and shoulders. Each of the electrical wires is electrically connected at one end to the electrically conductive fabric of one of the protruding nodules through the corresponding channel in the inner core structure and is electrically connected at the opposite end to the electrotherapeutic signal generator in order to receive the electrical nerve stimulation pulses generated by the electrotherapeutic signal generator and deliver those pulses through each of the protruding nodules to the corresponding portion of the person's head, neck, and shoulders. The outer covering is an enclosure made of a breathable fabric and is configured to enclose the entire inner core structure while exposing the protruding nodules.

Another objective of the present invention is to provide the foregoing device, with the outer covering further including two handles. Each of the handles is connected at one end to the outer covering at a position corresponding to the free end of one of the two side arms of the inner core structure. The opposite end of each of the handles is configured to be gripped by one of the person's hands in order to press the inner side of the posterior portion and the two side arms of the inner core structure more firmly against the person's neck and shoulders by means of the weight of the person's arms or elbow. Thus, not only is the person's neck given more support, but also the contact between the electrically conductive fabric of each of the protruding nodules and the skin of the person's neck or shoulders is effectively enhanced to intensify the stimulating effect of the electrical nerve stimulation pulses on the corresponding nerve and muscle groups in the person's neck and shoulders.

Still another objective of the present invention is to provide the foregoing device, with the outer covering further including a hood. The hood is connected at one end to a portion of the outer covering that corresponds to the posterior portion of the inner core structure. Moreover, the hood can be stored in the outer covering and also be taken out of the outer covering in order to be pulled over the person's head, thus effectively shielding the person's head from the disturbance of unnecessary images and sounds while keeping the person's head warm. The hood can be detached from the device and be used as a travel carry case for the device.

Yet another objective of the present invention is to provide the foregoing device, wherein the periphery of each of the protruding nodules is sewn to the outer covering at a position corresponding to the corresponding horizontal cushion opening. This technical feature allows the outer covering and the protruding nodules sewn thereto to be cleaned at the same time.

BRIEF DESCRIPTION OF THE SEVERAL VIEWS OF THE DRAWINGS

The objectives, technical features, and effects of the present invention will be described in more detail below with reference to some illustrative embodiments in conjunction with the accompanying drawings, in which.

DETAILED DESCRIPTION OF THE INVENTION

The inventor of the present invention has long been devoted to research and development in the field of medical assistive devices, and during the process has found the various drawbacks and inconveniences of use of the conventional medium-frequency electrotherapy devices as stated above. The inventor of the present invention then started conceiving a massage device that can perform electrotherapy on a person's head, neck, and shoulders. The goal was to provide the massage device with a compact, simple, and multifunctional structural design that allows the massage device to be carried around and easily operated by patients and physical therapists wherever desired. In addition, the massage device should be able to help a patient keep the natural lordotic curvature of the cervical spine while performing electrotherapeutic massage on the corresponding important nerve and muscle groups in the patient's head, neck, and shoulders, thereby enhancing the effect of the electrotherapeutic massage effectively, relieving pain from the aforesaid body parts efficiently as well as precisely, reducing the tightness of the related muscle groups, and by means of this muscle relaxing mechanism, fine-tuning the corresponding portion of the vertebral column to its proper position.

Figure 1:
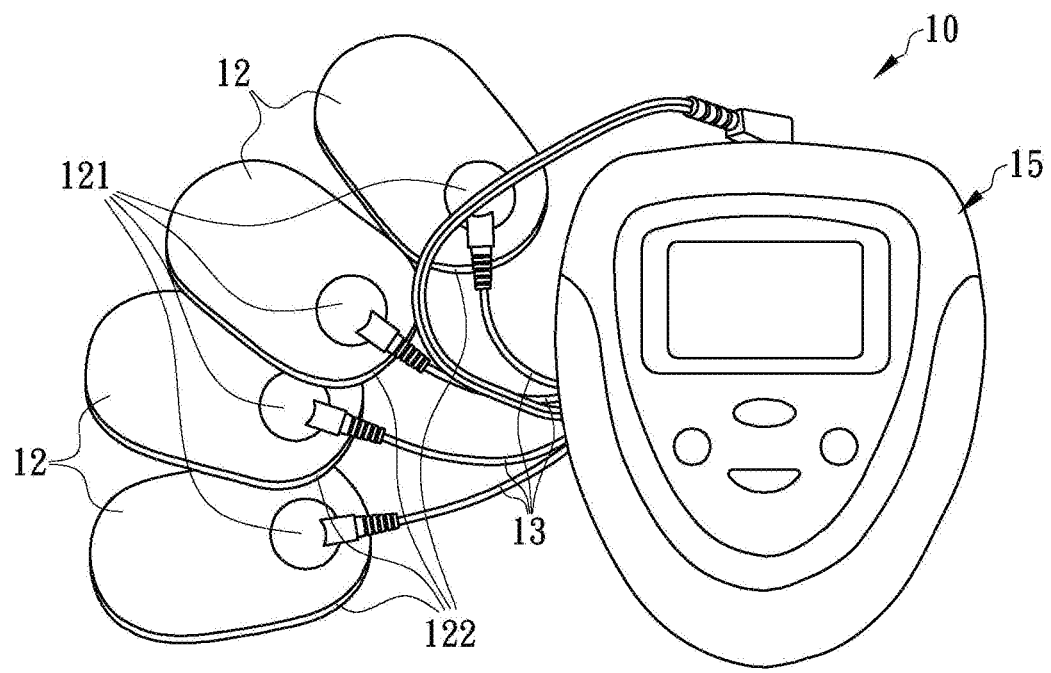
FIG. 1 is a perspective view of a conventional medium-frequency electrotherapy device.
Figure 1:
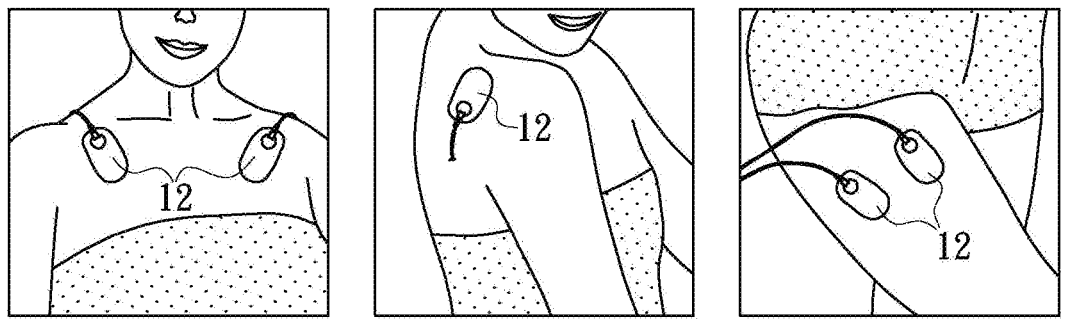
Figure 2:
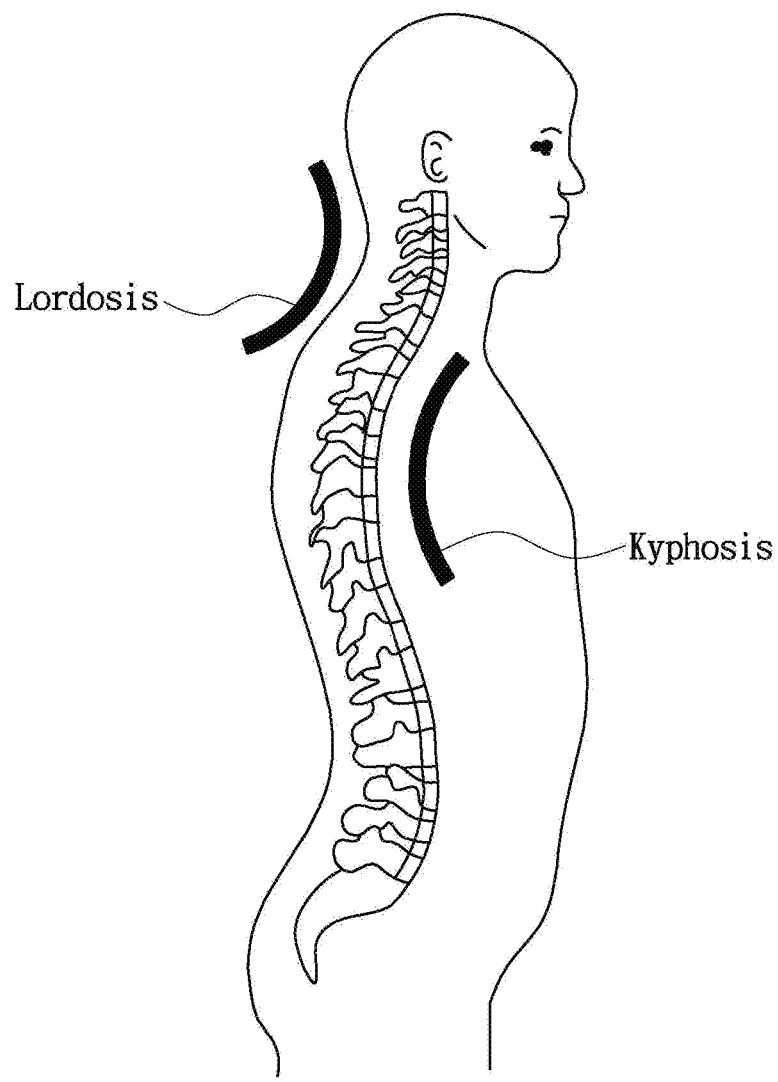
FIG. 2 is a side view of the human spine, showing in particular lordosis of the cervical vertebrae and kyphosis of the thoracic vertebrae.
Figure 3:
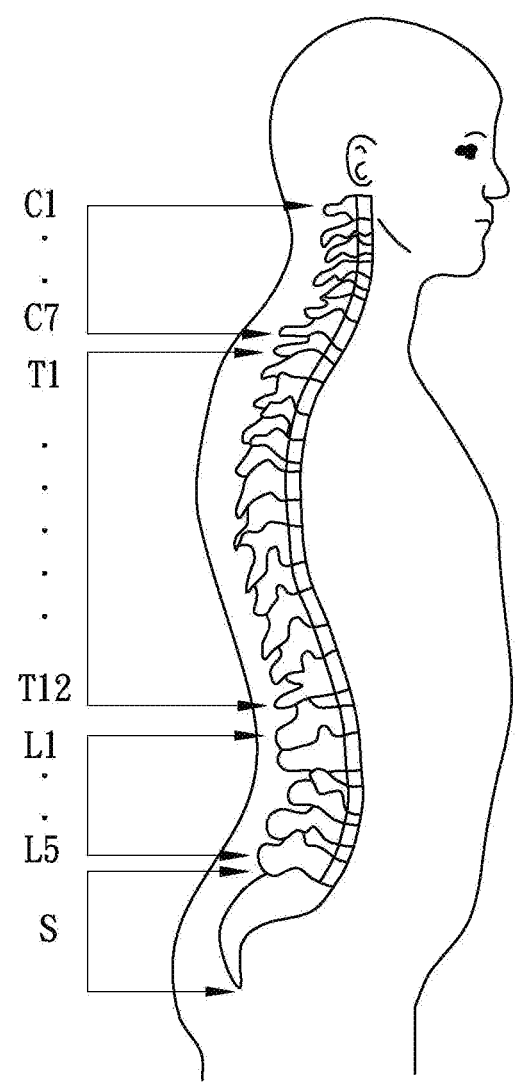
FIG. 3 is another side view of the human spine structure.
Figure 4:
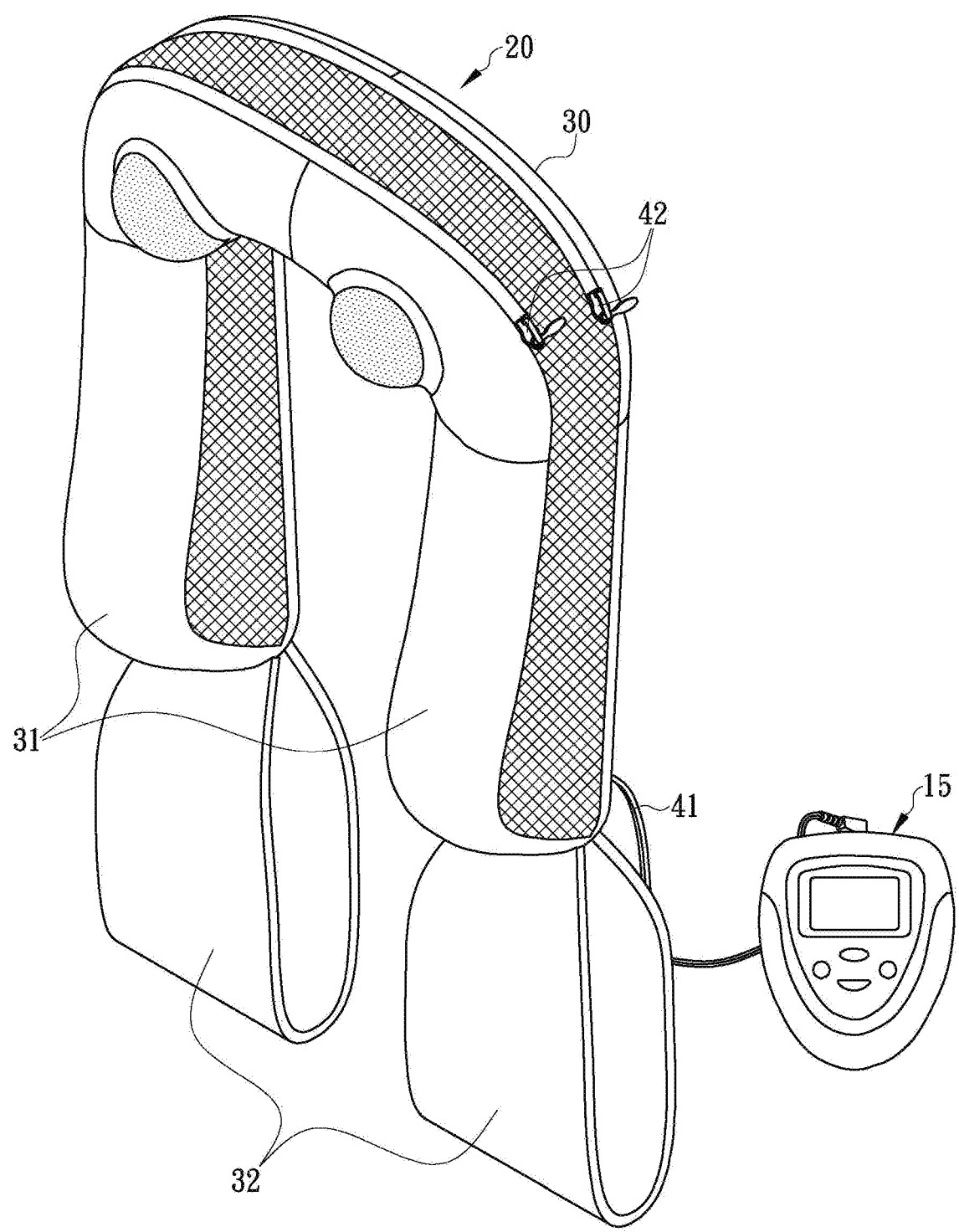
FIG. 4 is a perspective view of the electrotherapeutic massage device in a preferred embodiment of the present invention.

The present invention provides a device for performing electrotherapeutic massage on a person's head, neck, and shoulders. In a preferred embodiment of the invention, referring to FIGS. 4, 5, and 6, the electrotherapeutic massage device 20 is configured to be electrically connected to an electrotherapeutic signal generator 15, such as a transcutaneous electrical nerve stimulator (TENS) or electronic muscle stimulator (EMS), in order to receive the electrical nerve stimulation pulses generated by and sent from the electrotherapeutic signal generator 15 and deliver those pulses to the corresponding nerve and muscle groups in a patient's head, neck, and shoulders, thereby performing an effective electrotherapeutic massage on, and relieving pain precisely and efficiently from, the patient's aforesaid body parts. As shown in FIG. 4 and FIG. 6, the electrotherapeutic massage device 20 includes an inner core structure 21, at least four protruding nodules 24, a plurality of electrical wires 41, and an outer covering 30. The inner core structure 21, as shown in FIG. 6, is made of a special blend of foam materials and is formed with a horizontal accommodating opening 211 at the center. The horizontal accommodating opening 211 has a configuration matching the natural curvature and alignment of a patient's cervical vertebrae C1~C3. In addition, referring to FIG. 3 and FIG. 4, the horizontal accommodating opening 211 has an accommodating curvature matching the kyphotic curvature, or kyphosis, of a patient's thoracic vertebrae T1~T3. Thus, the horizontal accommodating opening 211 can accommodate a patient's neck both stably and comfortably, with the inner side of a posterior portion 22 of the inner core structure 21 lying against a supporting area of the patient's neck, and two side arms 23 of the inner core structure 21 pressed respectively against supporting areas of the patient's shoulders, wherein the posterior portion 22 is adjacent to the rear side of the inner core structure 21. When applied to a patient's neck and shoulders, the inner core structure 21 can be freely compressed or freely expand, allowing the patient's cervical spine (especially the cervical vertebrae C1, C2, and C7) to stay in a natural relaxed alignment by flexing and extending. This technical feature helps keep the natural lordotic curvature, or lordosis, of the cervical vertebrae C1~C7 during an electrotherapeutic massage session so that the effect of the electrotherapeutic massage can be effectively enhanced. Referring back to FIG. 6, the inner core structure 21 further includes at least two vertical cushion openings 212 and a plurality of horizontal cushion openings 213. The vertical cushion openings 212 are vertically formed in the posterior portion 22 of the inner core structure 21 to enable the posterior portion 22 of the inner core structure 21 to deform or be displaced in a forward or rearward direction so that, when the inner side of the posterior portion 22 of the inner core structure 21 is tightly pressed against a patient's neck, the inner core structure 21 can effectively absorb the pressure it applies to the neck. The horizontal cushion openings 213, on the other hand, are horizontally formed in each of the side arms 23 and the posterior portion 22 of the inner core structure 21 to provide the inner core structure 21 with sufficient ventilation. The horizontal cushion openings 213 not only ensure that a patient's neck will feel cool and comfortable when receiving electrotherapeutic massage, but also allow the side arms 23 and the posterior portion 22 to deform and be displaced arbitrarily in order to form a configuration that matches the contours of the patient's neck and shoulders and that therefore can produce an additional and comfortable cushioning and supporting effect on the patient's head, neck, and shoulders. With continued reference to FIG. 6, each protruding nodule 24 is made of an electrically conductive fabric and has a hardness higher than that of the inner core structure 21. The periphery of each protruding nodule 24 is sewn to the wall of, or embedded in, the corresponding horizontal cushion opening 213. The electrically conductive fabric of each protruding nodule 24 has one side protruding toward the horizontal accommodating opening 211 such that each protruding nodule 24 has a stable and robust configuration and can make comfortable contact with the skin of a patient's neck and shoulders to enable proper current conduction between the electrically conductive fabric and the skin of the patient's neck and shoulders, allowing the electrical nerve stimulation pulses received from the electrotherapeutic signal generator 15 to be delivered through the protruding nodules 24 to the corresponding portions of the patient's neck and shoulders, thereby relaxing the nerve and muscle groups in the corresponding portions of the patient's neck and shoulders and relieving pain from the patient's aforesaid body parts. Each electrical wire 41 has one end electrically connected to the electrically conductive fabric of the corresponding protruding nodule 24 through the corresponding channel in the inner core structure 21. The opposite end of each electrical wire 41 is electrically connected to the electrotherapeutic signal generator 15 in order to receive the electrical nerve stimulation pulses generated by and sent from the electrotherapeutic signal generator 15 and deliver the pulses through the corresponding protruding nodule 24 to the corresponding portion of the patient's head, neck, and shoulders. Thus, when the inner core structure 21 pushes the protruding nodules 24 and thereby presses the electrically conductive fabric of each protruding nodule 24 against the skin of the corresponding body portion, an effective electrotherapy as well as acupressure therapy is applied to the nerve and muscle groups and acupuncture points of those body portions. The outer covering 30 is an enclosure made of a breathable fabric and is configured to enclose the entire inner core structure 21 while exposing the protruding nodule 24.

In a preferred embodiment of the present invention, referring to FIG. 6, the inner core structure 21 is preferably made of a special blend of viscoelastic memory foam materials to ensure that the inner core structure 21 can always be mounted accurately in the outer covering 30 and be positioned, along with the outer covering 30, on the corresponding portions of a patient's neck and shoulders.

Figure 5:
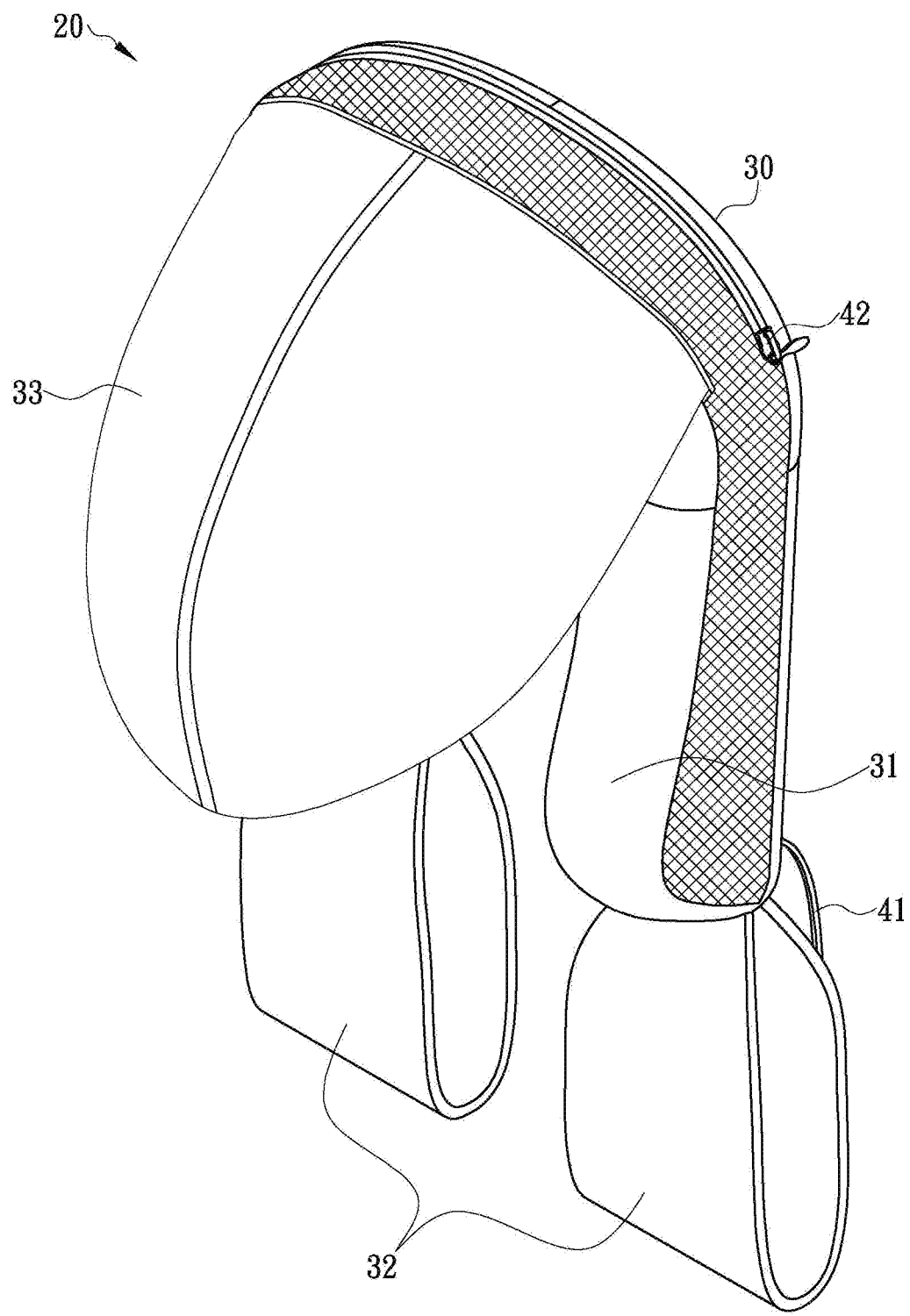
FIG. 5 is a perspective view of the electrotherapeutic massage device in another preferred embodiment of the present invention.
Figure 6:
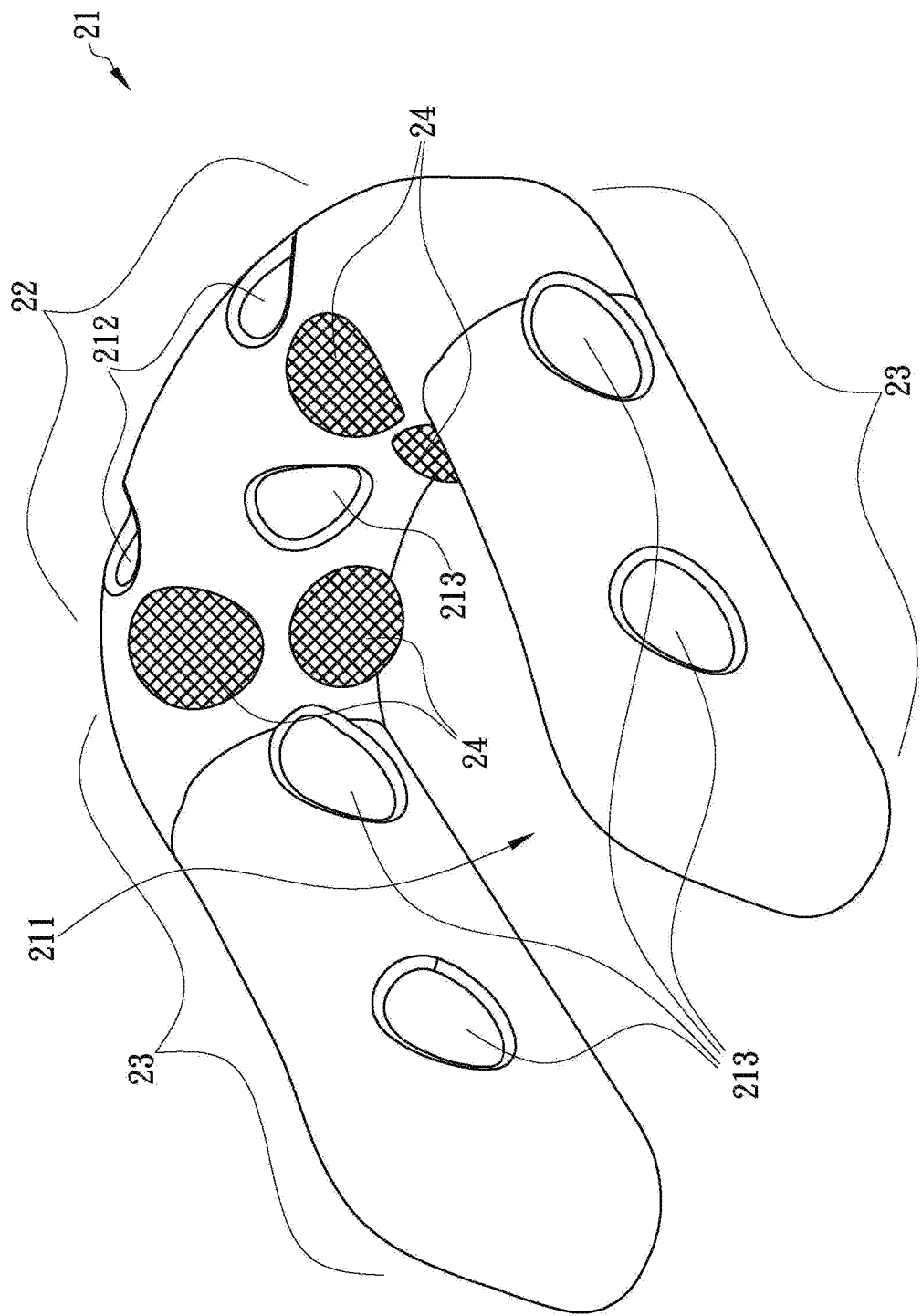
FIG. 6 is a perspective view of the inner core structure in the foregoing preferred embodiments of the present invention.

In another preferred embodiment of the present invention, referring to FIGS. 4, 5, and 6, the periphery of each protruding nodule 24 is sewn to the outer covering 30 at a position corresponding to the wall of the corresponding horizontal cushion opening 213 in the inner core structure 21. Thus, when the massage device becomes dirty after repeated use, the user can remove the outer covering 30 from the inner core structure 21 and clean the outer covering 30 together with the protruding nodules 24 sewn thereto.

In still another preferred embodiment of the present invention, referring to FIGS. 3, 4, 5, and 6, the protruding nodules 24 are respectively provided at positions corresponding to the cervical nerves C-1, C-2, and C-7 and the thoracic nerve 1 (T1), which emerge from the spine laterally between the person's upper thoracic spine portion and the suboccipitial region at which the posterior hairline is commonly positioned. Thus, when the inner core structure 21 pushes the protruding nodules 24 and thereby presses the electrically conductive fabric of each protruding nodule 24 against the skin of the corresponding portion, an effective electrotherapy as well as acupressure therapy is applied to the C-1, C-2, C-7, and T1 nerves and the adjacent acupuncture points.

In a further preferred embodiment of the present invention, referring to FIGS. 4, 5, and 6, the outer covering 30 is an enclosure made of a breathable fabric and encloses the entire inner core structure 21 while allowing the protruding nodules 24 to be exposed outside the outer covering 30. Moreover, when the two side arms 23 and the posterior portion 22 of the inner core structure 21 enclosed in the outer covering 30 and the outer covering 30 itself are pressed against a patient's neck and shoulders, the structure of the outer covering 30 provides a ventilating and cooling environment for the heat generated between the patient's neck and shoulders and the inner core structure 21. Besides, to facilitate identification of the inner core structure 21 and render the outer covering 30 more ductile, the outer covering 30 may be a breathable fabric enclosure made of a transparent or translucent plastic material and preferably has a mesh-like enclosure structure with at least one zipper 42 to make it easier to put the inner core structure 21 into the outer covering 30 and take the inner core structure 21 out of the outer covering 30.

In still another preferred embodiment of the present invention, referring to FIGS. 4, 5, and 6, the outer covering 30 further includes two handles 31. Each handle 31 has one end connected to the outer covering 30 at a position corresponding to the free end of one of the two side arms 23 of the inner core structure 21. The opposite end of each handle 31 is designed to be gripped by one of a patient's hands so that the inner side of the posterior portion 22 and the two side arms 23 of the inner core structure 21 can lie more firmly on the patient's neck and shoulders to not only provide more support for the patient's neck, but also enhance the contact between the electrically conductive fabric of each protruding nodule 24 and the skin of the patient's neck or shoulders effectively, thereby increasing the stimulating effect of the electrotherapeutic signals on the nerve and muscle groups in the patient's neck and shoulders. In addition, the outer covering 30 includes two loops 32 provided respectively at the ends of the handles 31 that correspond to the free ends of the side arms 23. A patient may extend their arms or elbows through the loops 32 respectively in order for the weight of the arms or elbows to bring the posterior portion 22 and the two side arms 23 of the inner core structure 21 into even securer in contact with the patient's neck and shoulders, thus not only providing even more support for the patient's neck, but also effectively enhancing the contact between the electrically conductive fabric of each protruding nodule 24 and the skin of the patient's neck or shoulders, thereby increasing the stimulating effect of the electrotherapeutic signals on the nerve and muscle groups in the patient's neck and shoulders. Moreover, by applying a pressure to the loops 32 and hence the inner core structure 21 manually, a patient can freely control and adjust the strength and type of the electrical nerve stimulation pulses of the electrotherapeutic signal generator 15 as needed.

In yet another preferred embodiment of the present invention, referring to FIG. 5, the outer covering 30 further includes a hood 33. The hood 33 has one end connected to a portion of the outer covering 30 that corresponds to the rear side of the posterior portion 22 of the inner core structure 21. The hood 33 can be stored in the outer covering 30 and, when taken out of the outer covering 30, can be pulled over a patient's head to keep the patient's head warm while also shielding the patient's head from the disturbance of unnecessary images and sounds, making it easier for the patient to stay in a tranquil and totally relaxed state while receiving an electrotherapeutic massage. The hood 33 can also be detached from the device 20 and be used as a travel carry case for the device 20.

According to the above, the electrotherapeutic massage device of the present invention is structurally simple, does not take up too much space, has a multifunctional structural design, can be easily operated by patients as well as physical therapist wherever desired, and can perform an effective electrotherapeutic massage precisely on the nerve and muscle groups under the corresponding important acupuncture points on a patient's head, neck, and shoulders without causing problems typical of the conventional electrotherapy devices, thus relieving pain precisely and efficiently from the patient's head, neck, and shoulder muscles and providing a muscle relaxing mechanism that allows the patient's corresponding cervical vertebrae and thoracic vertebrae to be fine-tuned to their proper positions.

The above-mentioned descriptions represent merely the exemplary embodiment of the present disclosure, without any intention to limit the scope of the present disclosure thereto. Various equivalent changes, alternations or modifications based on the claims of present disclosure are all consequently viewed as being embraced by the scope of the present disclosure.

What is claimed is:
1. A device for performing electrotherapeutic massage on a person's head, neck, and shoulders, wherein the device is electrically connectable to an electrotherapeutic signal generator in order to receive electrical nerve stimulation pulses generated by the electrotherapeutic signal generator and deliver the electrical nerve stimulation pulses to corresponding portions of the person's head, neck, and shoulders, thereby performing the electrotherapeutic massage effectively on the corresponding portions of the person's head, neck, and shoulders and relieving pain precisely from the person's head, neck, and shoulders, the electrotherapeutic signal generator being selected from the group consisting of a transcutaneous electrical nerve stimulator (TENS) and an electronic muscle stimulator (EMS), the device comprising:

an inner core structure made of a blend of foam materials and centrally formed with a horizontal accommodating opening, wherein the horizontal accommodating opening has a configuration matching a natural curvature and alignment of the person's cervical spine and has an accommodating curvature matching a kyphotic curvature of the person's thoracic vertebrae in order for the person's neck to be stably and comfortably accommodated in the horizontal accommodating opening; the inner core structure has a posterior portion adjacent to a rear side of the inner core structure; the posterior portion has an inner side configured to lie against a supporting area of the person's neck; the inner core structure further has two side arms configured to be pressed against supporting areas of the person's shoulders respectively; the inner core structure is configured to be freely compressed or freely expand during use in order for the person's cervical spine to flex, extend, and thereby maintain the natural alignment, and to also maintain a natural lordotic curvature when the electrotherapeutic massage is performed, thus effectively enhancing an effect of the electrotherapeutic massage on the person's head, neck, and shoulders; the inner core structure further comprises at least two vertical cushion openings and a plurality of horizontal cushion openings; the vertical cushion openings are vertically formed in the posterior portion of the inner core structure to enable forward or rearward deformation and displacement of the posterior portion of the inner core structure so that, when the inner side of the posterior portion of the inner core structure is pressed tightly against the person's neck, the inner core structure is able to effectively absorb a pressure applied thereby to the person's neck; and the horizontal cushion openings are horizontally formed in each of the side arms and the posterior portion of the inner core structure to not only enable sufficient ventilation through the inner core structure, thereby ensuring that the person's neck feels cool and comfortable when the electrotherapeutic massage is performed on the person, but also allow the side arms and the posterior portion to be deformed and displaced arbitrarily to form a configuration matching contours of the person's neck and shoulders, thereby providing additional and comfortable cushion and support for the person's head, neck, and shoulders;

at least four protruding nodules each made of an electrically conductive fabric, wherein the protruding nodules have a higher hardness than the inner core structure; each of the protruding nodules has a periphery sewn to a wall of, or embedded in, a corresponding one of the horizontal cushion openings; and each said electrically conductive fabric has a side protruding toward the horizontal accommodating opening such that each of the protruding nodules has a stable and robust configuration and is able to make comfortable contact with the skin of the person's neck, thus enabling proper current conduction between each said electrically conductive fabric and the skin of the person's neck, allowing the electrical nerve stimulation pulses received from the electrotherapeutic signal generator to be delivered through each of the protruding nodules to a corresponding portion of the person's neck to relax muscles in the corresponding portion of, and thereby relieve pain from, the person's neck;

a plurality of electrical wires each having an end electrically connected through a corresponding channel in the inner core structure to the electrically conductive fabric of one of the protruding nodules and an opposite end electrically connected to the electrotherapeutic signal generator in order to receive the electrical nerve stimulation pulses generated by and sent from the electrotherapeutic signal generator and deliver the electrical nerve stimulation pulses through each of the protruding nodules to the corresponding portion of the person's head, neck, and shoulders so that, when the inner core structure pushes the protruding nodules and thereby presses the electrically conductive fabric of each of the protruding nodules against the skin of the corresponding portion of the person's head, neck, and shoulders, an effective electrotherapy as well as acupressure therapy is applied to nerves and acupuncture points of each said corresponding portion of the person's head, neck, and shoulders; and an outer covering, which is an enclosure made of a breathable fabric and is configured to enclose the entire inner core structure while allowing exposure of the protruding nodules outside the outer covering.

2. The device of claim 1, wherein the foam materials are viscoelastic memory foam materials.

3. The device of claim 2, wherein the protruding nodules correspond in positions respectively to the cervical nerves C-1, C-2, and C-7 and the thoracic nerve T-1 on both sides of the spine, which emerge from the spine bilaterally and are located between the person's upper thoracic spine portion and suboccipital region at which posterior hairline is commonly located, so that, when the inner core structure pushes the protruding nodules and thereby presses the electrically conductive fabric of each of the protruding nodules against the skin of the corresponding portion of the person's head, neck, and shoulders, an effective electrotherapy as well as acupressure therapy is applied to the nerves and the acupuncture points of each said corresponding portion of the person's head, neck, and shoulders.

4. The device of claim 3, wherein the outer covering is structured to provide a ventilating and cooling environment for heat generated between the person's shoulders and neck and the inner core structure when the two side arms and the posterior portion of the inner core structure in the outer covering and the outer covering itself are pressed against the person's shoulders and neck.

5. The device of claim 3, wherein the outer covering is a breathable fabric enclosure made of a transparent or translucent plastic material.

6. The device of claim 5, wherein the outer covering comprises two handles, and each of the handles has a first end corresponding to a free end of one of the two side arms of the inner core structure, and a second end opposite to the first end and corresponding to an end of the side arm that is opposite to the free end and connected to the posterior portion, the second end being configured to be gripped by one of the person's hands in order to press the posterior portion and the two side arms of the inner core structure more firmly against the person's neck and shoulders, thus not only providing more support for the person's neck, but also effectively enhancing contact between the electrically conductive fabric of each of the protruding nodules and the skin of the person's neck or shoulders to intensify a stimulating effect of the electrical nerve stimulation pulses on corresponding nerve and muscle groups in the person's neck and shoulders.

7. The device of claim 6, wherein the outer covering further comprises two loops; each of the loops is provided at the first end of one of the handles so that the person's arms or elbows may extend through the loops respectively, allowing a weight of the person's arms or elbows to press the posterior portion and the two side arms of the inner core structure even more firmly against the person's neck and shoulders, thus not only providing even more support for the person's neck, but also effectively enhancing the contact between the electrically conductive fabric of each of the protruding nodules and the skin of the person's neck or shoulders to intensify the stimulating effect of the electrical nerve stimulation pulses on the corresponding nerve and muscle groups in the person's neck and shoulders; and by applying a pressure to the loops and hence the inner core structure manually, the person is able to manually and freely control and adjust a strength and type of the electrical nerve stimulation pulses generated by the electrotherapeutic signal generator according to the person's needs.

8. The device of claim 7, wherein the outer covering further comprises a hood, the hood has an end connected to a portion of the outer covering that corresponds to the posterior portion of the inner core structure, the hood is able to be stored in the outer covering and also to be taken out of the outer covering in order to be pulled over the person's head, thus keeping the person's head warm and effectively shielding the person's head from disturbance of unnecessary images and sounds, and the hood is further configured to be detached from the device and be used as a travel carry case for the device.

9. The device of claim 8, wherein the outer covering is mesh-like and is provided with at least one zipper to facilitate storage of the inner core structure or the hood in the outer covering.

10. The device of claim 1, wherein the protruding nodules correspond in positions respectively to the cervical nerves C-1, C-2, and C-7 and the thoracic nerve T-1 on both sides of the spine, which emerge from the spine bilaterally and are located between the person's upper thoracic spine portion and suboccipital region at which posterior hairline is commonly located, so that, when the inner core structure pushes the protruding nodules and thereby presses the electrically conductive fabric of each of the protruding nodules against the skin of the corresponding portion of the person's head, neck, and shoulders, an effective electrotherapy as well as acupressure therapy is applied to the nerves and the acupuncture points of each said corresponding portion of the person's head, neck, and shoulders.

11. The device of claim 10, wherein the outer covering is structured to provide a ventilating and cooling environment for heat generated between the person's shoulders and neck and the inner core structure when the two side arms and the posterior portion of the inner core structure in the outer covering and the outer covering itself are pressed against the person's shoulders and neck.

12. The device of claim 10, wherein the outer covering is a breathable fabric enclosure made of a transparent or translucent plastic material.

13. The device of claim 12, wherein the outer covering comprises two handles, and each of the handles has a first end corresponding to a free end of one of the two side arms of the inner core structure, and a second end opposite to the first end and corresponding to an end of the side arm that is opposite to the free end and connected to the posterior portion, the second end being configured to be gripped by one of the person's hands in order to press the posterior portion and the two side arms of the inner core structure more firmly against the person's neck and shoulders, thus not only providing more support for the person's neck, but also effectively enhancing contact between the electrically conductive fabric of each of the protruding nodules and the skin of the person's neck or shoulders to intensify a stimulating effect of the electrical nerve stimulation pulses on corresponding nerve and muscle groups in the person's neck and shoulders.

14. The device of claim 13, wherein the outer covering further comprises two loops; each of the loops is provided at the first end of one of the handles so that the person's arms or elbows may extend through the loops respectively, allowing a weight of the person's arms or elbows to press the posterior portion and the two side arms of the inner core structure even more firmly against the person's neck and shoulders, thus not only providing even more support for the person's neck, but also effectively enhancing the contact between the electrically conductive fabric of each of the protruding nodules and the skin of the person's neck or shoulders to intensify the stimulating effect of the electrical nerve stimulation pulses on the corresponding nerve and muscle groups in the person's neck and shoulders; and by applying a pressure to the loops and hence the inner core structure manually, the person is able to manually and freely control and adjust a strength and type of the electrical nerve stimulation pulses generated by the electrotherapeutic signal generator according to the person's needs.

15. The device of claim 14, wherein the outer covering further comprises a hood, the hood has an end connected to a portion of the outer covering that corresponds to the posterior portion of the inner core structure, the hood is able to be stored in the outer covering and also to be taken out of the outer covering in order to be pulled over the person's head, thus keeping the person's head warm and effectively shielding the person's head from disturbance of unnecessary images and sounds, and the hood is further configured to be detached from the device and be used as a travel carry case for the device.

16. The device of claim 15, wherein the outer covering is mesh-like and is provided with at least one zipper to facilitate storage of the inner core structure or the hood in the outer covering.

17. A device for performing electrotherapeutic massage on a person's head, neck, and shoulders, wherein the device is electrically connectable to an electrotherapeutic signal generator in order to receive electrical nerve stimulation pulses generated by the electrotherapeutic signal generator and deliver the electrical nerve stimulation pulses to corresponding portions of the person's head, neck, and shoulders, thereby performing the electrotherapeutic massage effectively on the corresponding portions of the person's head, neck, and shoulders and relieving pain precisely from the person's head, neck, and shoulders, the electrotherapeutic signal generator being selected from the group consisting of a transcutaneous electrical nerve stimulator (TENS) and an electronic muscle stimulator (EMS), the device comprising:

an inner core structure made of a blend of foam materials and centrally formed with a horizontal accommodating opening, wherein the horizontal accommodating opening has a configuration matching a natural curvature and alignment of the person's cervical spine and has an accommodating curvature matching a kyphotic curvature of the person's thoracic vertebrae in order for the person's neck to be stably and comfortably accommodated in the horizontal accommodating opening; the inner core structure has a posterior portion adjacent to a rear side of the inner core structure; the posterior portion has an inner side configured to lie against a supporting area of the person's neck; the inner core structure further has two side arms configured to be pressed against supporting areas of the person's shoulders respectively; the inner core structure is configured to be freely compressed or freely expand during use in order for the person's cervical spine to flex, extend, and thereby maintain the natural alignment, and to also maintain a natural lordotic curvature when the electrotherapeutic massage is performed, thus effectively enhancing an effect of the electrotherapeutic massage on the person's head, neck, and shoulders; the inner core structure further comprises at least two vertical cushion openings and a plurality of horizontal cushion openings; the vertical cushion openings are vertically formed in the posterior portion of the inner core structure to enable forward or rearward deformation and displacement of the posterior portion of the inner core structure so that, when the inner side of the posterior portion of the inner core structure is pressed tightly against the person's neck, the inner core structure is able to effectively absorb a pressure applied thereby to the person's neck; and the horizontal cushion openings are horizontally formed in each of the side arms and the posterior portion of the inner core structure to not only enable sufficient ventilation through the inner core structure, thereby ensuring that the person's neck feels cool and comfortable when the electrotherapeutic massage is performed on the person, but also allow the side arms and the posterior portion to be deformed and displaced arbitrarily to form a configuration matching contours of the person's neck and shoulders, thereby providing additional and comfortable cushion and support for the person's head, neck, and shoulders;

at least four protruding nodules each made of an electrically conductive fabric, wherein the protruding nodules have a higher hardness than the inner core structure; and each said electrically conductive fabric has a side protruding toward the horizontal accommodating opening such that each of the protruding nodules has a stable and robust configuration and is able to make comfortable contact with the skin of the person's neck, thus enabling proper current conduction between each said electrically conductive fabric and the skin of the person's neck, allowing the electrical nerve stimulation pulses received from the electrotherapeutic signal generator to be delivered through each of the protruding nodules to a corresponding portion of the person's neck to relax muscles in the corresponding portion of, and thereby relieve pain from, the person's neck;

a plurality of electrical wires each having an end electrically connected through a corresponding channel in the inner core structure to the electrically conductive fabric of one of the protruding nodules and an opposite end electrically connected to the electrotherapeutic signal generator in order to receive the electrical nerve stimulation pulses generated by and sent from the electrotherapeutic signal generator and deliver the electrical nerve stimulation pulses through each of the protruding nodules to the corresponding portion of the person's head, neck, and shoulders so that, when the inner core structure pushes the protruding nodules and thereby presses the electrically conductive fabric of each of the protruding nodules against the skin of the corresponding portion of the person's head, neck, and shoulders, an effective electrotherapy as well as acupressure therapy is applied to nerves and acupuncture points of each said corresponding portion of the person's head, neck, and shoulders; and an outer covering, which is an enclosure made of a breathable fabric and is configured to enclose the entire inner core structure while allowing exposure of the protruding nodules outside the outer covering, wherein a periphery of each of the protruding nodules is sewn to the outer covering at a position corresponding to a wall of a corresponding one of the horizontal cushion openings.

18. The device of claim 17, wherein the protruding nodules correspond in positions respectively to the cervical nerves C-1, C-2, and C-7 and the thoracic nerve T-1 on both sides of the spine, which emerge from the spine bilaterally and are located between the person's upper thoracic spine portion and suboccipital region at which posterior hairline is commonly located, so that, when the inner core structure pushes the protruding nodules and thereby presses the electrically conductive fabric of each of the protruding nodules against the skin of the corresponding portion of the person's head, neck, and shoulders, an effective electrotherapy as well as acupressure therapy is applied to the nerves and the acupuncture points of each said corresponding portion of the person's head, neck, and shoulders.

19. The device of claim 18, wherein the outer covering is structured to provide a ventilating and cooling environment for heat generated between the person's shoulders and neck and the inner core structure when the two side arms and the posterior portion of the inner core structure in the outer covering and the outer covering itself are pressed against the person's shoulders and neck.

20. The device of claim 18, wherein the outer covering is a breathable fabric enclosure made of a transparent or translucent plastic material.

21. The device of claim 20, wherein the outer covering comprises two handles, and each of the handles has a first end corresponding to a free end of one of the two side arms of the inner core structure, and a second end opposite to the first end and corresponding to an end of the side arm that is opposite to the free end and connected to the posterior portion, the second end being configured to be gripped by one of the person's hands in order to press the posterior portion and the two side arms of the inner core structure more firmly against the person's neck and shoulders, thus not only providing more support for the person's neck, but also effectively enhancing contact between the electrically conductive fabric of each of the protruding nodules and the skin of the person's neck or shoulders to intensify a stimulating effect of the electrical nerve stimulation pulses on corresponding nerve and muscle groups in the person's neck and shoulders.

22. The device of claim 21, wherein the outer covering further comprises two loops; each of the loops is provided at the first end of one of the handles so that the person's arms or elbows may extend through the loops respectively, allowing a weight of the person's arms or elbows to press the posterior portion and the two side arms of the inner core structure even more firmly against the person's neck and shoulders, thus not only providing even more support for the person's neck, but also effectively enhancing the contact between the electrically conductive fabric of each of the protruding nodules and the skin of the person's neck or shoulders to intensify the stimulating effect of the electrical nerve stimulation pulses on the corresponding nerve and muscle groups in the person's neck and shoulders; and by applying a pressure to the loops and hence the inner core structure manually, the person is able to manually and freely control and adjust a strength and type of the electrical nerve stimulation pulses generated by the electrotherapeutic signal generator according to the person's needs.

23. The device of claim 22, wherein the outer covering further comprises a hood, the hood has an end connected to a portion of the outer covering that corresponds to the posterior portion of the inner core structure, the hood is able to be stored in the outer covering and also to be taken out of the outer covering in order to be pulled over the person's head, thus keeping the person's head warm and effectively shielding the person's head from disturbance of unnecessary images and sounds, and the hood is further configured to be detached from the device and be used as a travel carry case for the device.

24. The device of claim 23, wherein the outer covering is mesh-like and is provided with at least one zipper to facilitate storage of the inner core structure or the hood in the outer covering.

* * * * *